US011364087B2

(12) United States Patent
Moldon et al.

(10) Patent No.: US 11,364,087 B2
(45) Date of Patent: Jun. 21, 2022

(54) APPARATUS FOR POSITIONING A BREAST FOR RADIATION TREATMENT

(71) Applicant: PROVINCIAL HEALTH SERVICES AUTHORITY, Vancouver (CA)

(72) Inventors: Cheryl Moldon, Vancouver (CA); Scott Young, Vancouver (CA); Robin Coope, Vancouver (CA); Tania Arora, Vancouver (CA); Keri Smith, Vancouver (CA); Christina Cumayas, North Vancouver (CA); Bradford Gill, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 461 days.

(21) Appl. No.: 16/487,694

(22) PCT Filed: Feb. 28, 2018

(86) PCT No.: PCT/CA2018/050233
§ 371 (c)(1),
(2) Date: Aug. 21, 2019

(87) PCT Pub. No.: WO2018/157246
PCT Pub. Date: Sep. 7, 2018

(65) Prior Publication Data
US 2019/0388176 A1    Dec. 26, 2019

Related U.S. Application Data

(60) Provisional application No. 62/464,941, filed on Feb. 28, 2017.

(51) Int. Cl.
*A61B 90/17*    (2016.01)
*A61G 13/10*    (2006.01)
(Continued)

(52) U.S. Cl.
CPC .......... *A61B 90/17* (2016.02); *A61G 13/101* (2013.01); *A61N 5/10* (2013.01);
(Continued)

(58) Field of Classification Search
CPC ... A61B 90/17; A61B 6/04; A61B 2090/3966; A61B 2090/0817; A61B 2090/101;
(Continued)

(56) References Cited

U.S. PATENT DOCUMENTS 5,564,438 A    10/1996  Merchant
5,769,779 A *   6/1998  Alderson ............. A61N 5/1048
                                                     600/1
(Continued)

FOREIGN PATENT DOCUMENTS

EP      2675306 B1      8/2016
WO   2013050965 A1      4/2013
WO   2015013806 A1      2/2015

OTHER PUBLICATIONS

Probst, H. et al., "A systematic review of methods to immobilise breast tissue during adjuvant breast irradiation", Radiography 20 (2014) 70-81.
(Continued)

*Primary Examiner* — Christine H Matthews
*Assistant Examiner* — Joshua Daryl D Lannu
(74) *Attorney, Agent, or Firm* — Oyen Wiggs Green & Mutala LLP

(57) ABSTRACT

The present invention provides a method and apparatus to decrease acute and late skin toxicity for breast cancer patients undergoing radiation therapy. This invention will enable better breast positioning during therapy, eliminating skin folds and reducing the skin dose below that required for development of moist desquamation. The present invention has the potential to reduce the volume of normal tissue and organs at risk of being irradiated during a course of whole breast radiation therapy.

28 Claims, 13 Drawing Sheets

(51) Int. Cl.
*A61N 5/10* (2006.01)
*A61B 90/00* (2016.01)
*A61B 90/10* (2016.01)

(52) U.S. Cl.
CPC .......... *A61B 2090/0808* (2016.02); *A61B 2090/0817* (2016.02); *A61B 2090/101* (2016.02); *A61B 2090/3966* (2016.02); *A61N 2005/1091* (2013.01); *A61N 2005/1097* (2013.01)

(58) Field of Classification Search
CPC .......... A61B 2090/0808; A61N 5/1049; A61N 2005/1091; A61N 2005/1097; A61N 5/10; A61G 13/101
See application file for complete search history.

(56) References Cited

U.S. PATENT DOCUMENTS

| | | | |
|---|---|---|---|
| 6,589,254 B2* | 7/2003 | Fontenot | A61B 90/17 600/231 |
| 6,974,255 B1 | 12/2005 | Hixson, Sr. | |
| 7,597,104 B2 | 10/2009 | Zheng et al. | |
| 7,746,975 B2 | 6/2010 | Kashiwagi | |
| 7,763,864 B2 | 7/2010 | Formenti | |
| 7,828,744 B2* | 11/2010 | Rioux | A61B 90/11 600/562 |
| 7,940,891 B2 | 5/2011 | Star-Lack et al. | |
| 8,210,899 B2 | 7/2012 | Bush | |
| 8,218,723 B2 | 7/2012 | Ein-Gal | |
| 8,272,088 B2 | 9/2012 | Sliski et al. | |
| 8,523,630 B2 | 9/2013 | Bush | |
| 8,753,171 B2 | 6/2014 | Thompson | |
| 8,788,017 B2 | 7/2014 | Yu et al. | |
| 8,814,774 B2 | 8/2014 | Thompson | |
| 9,022,833 B2 | 5/2015 | Deming | |
| 9,084,886 B2 | 7/2015 | Bush | |
| 9,277,963 B2 | 3/2016 | Thompson | |
| 2002/0121273 A1 | 9/2002 | Nyilas | |
| 2006/0185087 A1 | 8/2006 | Coppens et al. | |
| 2007/0276229 A1 | 11/2007 | Adler | |
| 2011/0195634 A1 | 8/2011 | Flesch | |
| 2014/0121499 A1 | 5/2014 | Coppens et al. | |
| 2015/0164725 A1* | 6/2015 | Wilson | A61G 13/129 128/845 |
| 2015/0272682 A1 | 10/2015 | Sheng | |

OTHER PUBLICATIONS

Barrett-Lennard, M.J. et al., "Comparing immobilisation methods for the tangential treatment of large pendulous breasts", The Radiographer 2008; 55(2).
Almberg, S.S. et al., "Superficial doses in breast cancer radiotherapy using conventional and IMRT techniques: A film-based phantom study", Radiotherapy and Oncology. 2011;100(2):259-264.
Arenas, M. et al., "Do breast cups improve breast cancer dosimetry? A comparative study for patients with large or pendulous breasts", Acta Oncol. 2014;53(6):795-801.
Bentel, G.C. et al., "Acute and late morbidity of using a breast positioning ring in women with large/pendulous breasts", Radiotherapy and Oncology 1999;50(3):277-281.
Cheung, T. et al., "Multilayer Gafchromic film detectors for breast skin dose determination in vivo", Phys Med Biol. 2002;47(2):N31-N37.
Cohen, R. et al., "Effect of Bra use during Radiotherapy for Large Breasted Women: Acute Toxicity and Treated Heart and Lung Volume", Int J Radiat Oncol Biol Phys. 2008;72(1):S182-3.
Cox, J.D. et al., "Toxicity Criteria of the Radiation Therapy Oncology Group (RTOG) and the European Organization for Research and Treatment of Cancer (EORTC)", Int J Radiat Oncol Biol Phys 1995;31:1341-1346.
Fisher, B. et al., "Twenty-year follow-up of a randomized trial comparing total mastectomy, lumpectomy, and lumpectomy plus irradiation for the treatment of invasive breast cancer", N Engl J Med 2002;347:1233-1241.
Gray, J.R. et al., "Primary breast irradiation in large-breasted or heavy women: Analysis of cosmetic outcome", Int J Radiat Oncol Biol Phys. 1991;21(2):347-354.
Joseph, K. et al., "Cardiac-sparing radiation therapy using positioning breast shell for patients with left-sided breast cancer who are ineligible for breath-hold techniques", Advances in Radiation Oncology 2017, 2 p. 532-539.
Harper, J.L. et al., "Skin Toxicity During Breast Irradiation: Pathophysiology and Management", South Med J. 2004;97:989-993.
Hymes, S.R. et al., "Radiation dermatitis: Clinical presentation, pathophysiology, and treatment 2006", J Am Acad Dermatol. 2006;54:28-46.
Halkett, G.K.B. et al., "'If we get too close to your bones they'll go brittle': women's initial fears about radiotherapy for early breast cancer", Psycho-Oncol. 2008;17:877-884.
Kedge, M., "A systematic review to investigate the effectiveness and acceptability of interventions for moist desquamation in radiotherapy patients", Radiography (2009) 15, 247-257.
Kraus-Tiefenbacher, U. et al., "Factors of influence on acute skin toxicity of breast cancer patients treated with standard three-dimensional conformal radiotherapy (3D-CRT) after breast conserving surgery (BCS)", Radiation Oncology. 2012;7:217.
Lee, J., et al., "Patient-reported symptoms of radiation dermatitis during breast cancer radiotherapy: a pilot study", Qual Life Res, 2017 26:1713-1719.
Michalski, A. et al., "A dosimetric comparison of 3D-CRT, IMRT, and static tomotherapy with an SIB for large and small breast volumes", Medical Dosimetry. 2014;39(2):163-168.
Mulliez, T. et al., "Hypofractionated whole breast irradiation for patients with large breasts: A randomized trial comparing prone and supine positions", Radiotherapy and Oncology. 2013;108(2):203-208.
Pignol, J.-P. et al., "A Multicenter Randomized Trial of Breast Intensity—Modulated Radiation Therapy to Reduce Acute Radiation Dermatitis", J Clin Oncol., May 1, 2008, vol. 26, No. 13, 2085-2092.
Porock, D. et al., "Predicting the Severity of Radiation Skin Reactions in Women With Breast Cancer", Oncol Nurs Forum 1998;25:1019-1029.
Schnur, J.B. et al., "A Qualitative Analysis of Acute Skin Toxicity among Breast Cancer Radiotherapy Patients", Psychooncology. 2011;20(3):260-268. doi:10.1002/pon.1734.
Schnur, J.B. et al., "Breast Cancer Patients' Experience of External-Beam Radiotherapy", Qual Health Res. 2009;19:668-676.
Sun, L.-M. et al., "Evaluation the consistency of location of moist desquamation and skin high dose area for breast cancer patients receiving adjuvant radiotherapy after breast conservative surgery", Radiation Oncology. 2013;8(1):50.
Veronesi, U. et al., "Twenty-Year Follow-up of a Randomized Study Comparing Breast-Conserving Surgery with Radical Mastectomy for Early Breast Cancer", N Engl J Med 2002;347:1227-1232.
Wengstrom, Y. et al., "Perceived symptoms and quality of life in women with breast cancer receiving radiation therapy", Eur J Oncol Nurs. 2000;4:78-88.
Wright, J.L. et al., "Prospective evaluation of radiation-induced skin toxicity in a race/ethnically diverse breast cancer population", Cancer Medicine 2016; 5(3):454-464.
Varga, Z. et al., "Individual Positioning: A Comparative Study of Adjuvant Breast Radiotherapy in the Prone Versus Supine Position", Int J Radiat Oncol Biol Phys. 2009;75(1):94-100.

* cited by examiner

APPARATUS FOR POSITIONING A BREAST FOR RADIATION TREATMENT

CROSS-REFERENCE TO RELATED APPLICATIONS

This application claims priority from U.S. application No. 62/464,941 filed 28 Feb. 2017. For purposes of the United States, this application claims the benefit under 35 U.S.C. § 119 of U.S. application No. 62/464,941 filed 28 Feb. 2017 and entitled BREAST POSITIONING DEVICE FOR RADIOTHERAPY which is hereby incorporated herein by reference for all purposes.

FIELD

This invention relates to medical apparatus and in particular to apparatus useful for positioning a human breast to receive radiation treatment.

BACKGROUND

Breast cancer is common around the world. Breast cancer often commences with the formation of abnormal cells in milk ducts in the breast (ductal carcinoma-in-situ or DCIS). Left untreated, DCIS can progress to invasive breast cancer.

Radiation therapy is frequently used as part of the standard management for patients with ductal carcinoma-in-situ or with stage I or II invasive breast cancer. Approximately 50% of women with breast cancer receive radiation therapy. The radiation therapy typically involves delivering radiation to the whole breast.

Acute radio-dermatitis is a frequent complication of whole breast radiation therapy. Approximately 60% to 80% of all breast patients undergoing whole breast radiation therapy experience RTOG grade II or higher skin toxicity and 15% to 40% experience moist desquamation. Acute radio-dermatitis tends to occur especially in the infra-mammary skin fold and axilla regions especially in women with large and/or pendulous breasts. Acute skin reactions may range from mild erythema through to severe erythema, and may also include dry desquamation, moist desquamation and, rarely, ulceration or tissue necrosis.

Acute radio-dermatitis is a significant problem. This is because radio-dermatitis can cause significant discomfort, pain, increased rates of infection as well as long-term cosmetic changes. The extent to which patients suffer at home may not be observed or fully reported since the severity of reactions caused by radiation treatment may peak after treatment has been concluded. Severe skin reactions may also have psycho-social consequences for patients and impact the perception of radiotherapy in society at large. Previous qualitative research suggests that prior to radiotherapy treatment, "getting burnt," is a source of worry for women with breast cancer. The negative message that radiation therapy causes severe burns may discourage some women from seeking or consenting to potentially life-saving treatment.

Acute skin reactions progress throughout the course of radiation treatment and for the week following completion of therapy, after which resolution occurs. Skin toxicity generally peaks after the patient has completed the course of radiation treatment. Progressive depletion of stem cells within the basal layer of the epidermis occurs as a result of absorption of radiation dose. This depletion of cells and resultant inflammatory and infective processes is the underlying cause of acute radio-dermatitis.

Late effects of radiation on skin may occur months following treatment and generally affect breast cosmesis. Late effects are a result of dose to the dermal layer containing skin vasculature.

Due to the bolus effect of skin apposition, friction, and predisposition to infection of this area, skin reactions tend to be more marked in women with larger and/or more pendulous breasts. There is some degree of acceptance today that moist desquamation is unavoidable for larger breasted patients undergoing breast cancer treatment.

Positioning the breast during radiation treatment is a challenging problem which is exacerbated by the great variation in the size and shape of women's breasts. Breast volumes may be as large as 3 or 4 liters and breast tissue is often too heavy to be supported effectively using conventional approaches such as a standard brassiere or adhesive tape.

Various attempts have been made to reduce the incidence or severity of acute radio-dermatitis. For example:
  Many studies have looked at treating the skin with various agents to reduce reactions during or after therapy. Limited degrees of success have been achieved in this respect.
  Intensity modulated radiation therapy (IMRT) allows reduction of local hot spots within the breast. Such hot spots can occur due to variations in breast thickness along the path of the beam. Although IMRT works well to improve the homogeneity of dose within the target, it does not address the problem of high dose in skin folds. Only a marginal improvement in skin toxicity has been attributed to IMRT. IMRT is also not available in many developing countries where breast radiation treatment is administered. Older 3D conformal techniques can result in skin folds lying directly within higher dose regions (≥100% of the target dose), thus exacerbating the problem of moist desquamation.
  Prone patient positioning, whereby the patient lies face down on a specialized treatment couch with the breast hanging below, is another technique that has been tried. While prone positioning may eliminate skin folds for some patients, it is known to introduce additional problems such as reduced target coverage and is not a viable option for the majority of patients. Prone breast positioning has not been widely adopted.
  Various devices have been proposed for immobilizing breast tissue during irradiation. Devices that have been suggested include a standard brassiere, plastic breast cups, plastic rings, thermoformed plastic supports and others. Some of these devices require custom forming or fitting to a patient which can be time consuming. Further, for at least some of these devices there is a lack of evidence to indicate that the devices make a clinical difference in outcome.

Most commonly patients are placed on an angled support board such that the breast sits on the chest wall in a reasonably stable position. Requirements are that the position be comfortable and reproducible with arms and chin out of the way. For larger and more pendulous breasts, skin folds commonly exist as the breast falls either toward the abdomen or laterally toward the axilla and it is in these areas that the highest rates of skin toxicity are observed.

A tangential pair of radiation beams is used to cover the entire breast with 1.5 to 2 cm margins all around. For treatment of the patient's left breast this usually results in radiation being delivered to parts of the patient's left lung and heart. When breast tissue sags and skin folds are present, the radiation field borders are often extended inferiorly or laterally in order to include all of the breast tissue.

The following references provide more background to the present technology:
1. Almberg S S, Lindmo T, Frengen J. Superficial doses in breast cancer radiotherapy using conventional and IMRT techniques: A film-based phantom study. Radiotherapy and Oncology. 2011; 100 (2):259-64
2. Arenas M, Hernández V, Farrús B, Müller K, Gascón M, Pardo A, et al. Do breast cups improve breast cancer dosimetry? A comparative study for patients with large or pendulous breasts. Acta Oncol. 2014; 53 (6):795-801.
3. Bentel G C, Marks L B, Whiddon C S, Prosnitz L R. Acute and late morbidity of using a breast positioning ring in women with large/pendulous breasts. Radiotherapy and Oncology. 1999; 50 (3):277-81.
4. Cheung T, Butson M J, Yu P K N. Multilayer Gafchromic film detectors for breast skin dose determination in vivo. Phys Med Biol. 2002; 47 (2):N31-7
5. Cohen R, Freedman G, Li T, Li L, Brennan C, Anderson P, et al. Effect of Bra use during Radiotherapy for Large Breasted Women: Acute Toxicity and Treated Heart and Lung Volume. Int J Radiat Oncol Biol Phys. 2008; 72 (1):5182-3.
6. Cox J D, Stetz J and Pajak T F. Toxicity criteria of the Radiation Therapy Oncology Group (RTOG) and the European Organization for Research and Treatment of Cancer (EORTC). Int J Radiat Oncol Biol Phys 1995; 31:1341-1346.
7. Fisher B, Anderson S, Bryant J et al. Twenty-year follow-up of a randomized trial comparing total mastectomy, lumpectomy, and lumpectomy plus irradiation for the treatment of invasive breast cancer. N Engl J Med 2002; 347:1233-1241.
8. Gray J R, McCormick B, Cox L, Yahalom J. Primary breast irradiation in large-breasted or heavy women: Analysis of cosmetic outcome. Int J Radiat Oncol Biol Phys. 1991; 21 (2):347-54.
9. Joseph K et al., Cardiac-sparing radiation therapy using positioning breast shell for patients with left-sided breast cancer who are ineligible for breath-hold techniques. Advances in Radiation Oncology 2017, 2 p 532-539.
10. Harper J L, Franklin L E, Jenrette J M, Aguero E G. Skin toxicity during breast irradiation: pathophysiology and management. South Med J. 2004; 97:989-993.
11. Hymes S R, Strom E A, Fife C. Radiation dermatitis: clinical presentation, pathophysiology, and treatment 2006. J Am Acad Dermatol. 2006; 54:28-46.
12. Halkett G K, Kristjanson L J, Lobb E A. 'If we get too close to your bones they'll go brittle': women's initial fears about radiotherapy for early breast cancer. Psycho-Oncol. 2008; 17:877-884.
13. Kedge, E, M. (2009). A systematic review to investigate the effectiveness and acceptability of interventions for moist desquamation in radiotherapy patients, Radiography, 15, 247-257.
14. Kraus-Tiefenbacher U, Sfintizky A, Welzel G, Simeonova A, Sperk E, Siebenlist K, et al. Factors of influence on acute skin toxicity of breast cancer patients treated with standard three-dimensional conformal radiotherapy (3D-CRT) after breast conserving surgery (BCS). Radiation Oncology. 2012; 7:217.
15. Lee J, et al, Patient-reported symptoms of radiation dermatitis during breast cancer radiotherapy: a pilot study. Qual Life Res, 2017 26:1713-1719
16. Michalski A, Atyeo J, Cox J, Rinks M, Morgia M, Lamoury G. A dosimetric comparison of 3D-CRT, IMRT, and static tomotherapy with an SIB for large and small breast volumes. Medical Dosimetry. 2014; 39 (2) 163-8.
17. Mulliez T, Veldeman L, van Greveling A, Speleers B, Sadeghi S, Berwouts D, et al. Hypofractionated whole breast irradiation for patients with large breasts: A randomized trial comparing prone and supine positions. Radiotherapy and Oncology. 2013; 108 (2):203-8.
18. Pignol J P, Olivotto I, Rakovitch E, Gardner S, Sixel K, Beckham W, Vu T T, Truong P, Ackerman I, Paszat L. A multicenter randomized trial of breast intensity-modulated radiation therapy to reduce acute radiation dermatitis. J Clin Oncol. 2008 May 1; 26 (13):2085-92.
19. Probst H, Bragg C, Dodwell D, Green D, Hart J. A systematic review of methods to immobilise breast tissue during adjuvant breast irradiation. Radiography. 2013; 2014; 20 (1):70.
20. Porock D, Kristjanson L, Nikoletti S, Cameron F and Pedler P. Predicting the severity of radiation skin reactions in women with breast cancer. Oncol Nurs Forum 1998; 25:1019-1029.
21. Schnur J B, Ouellette S C, DiLorenzo T A, Green S, Montgomery G H. A Qualitative Analysis of Acute Skin Toxicity among Breast Cancer Radiotherapy Patients. *Psycho-oncology.* 2011; 20 (3):260-268. doi:10.1002/pon.1734.
22. Schnur J B, Ouellette S C, Bovbjerg D H, Montgomery G H. Breast cancer patients' experience of external-beam radiotherapy. Qual Health Res. 2009; 19:668-676.
23. Sun L, Huang E, Liang J, Meng F, Chang G, Tsao M. Evaluation the consistency of location of moist desquamation and skin high dose area for breast cancer patients receiving adjuvant radiotherapy after breast conservative surgery. Radiation Oncology. 2013; 8 (1):50.
24. Veronesi U C N, Mariani L, Greco M, Saccozzi R, Luini A, et al. Twenty-Year Follow-up of a Randomized Study Comparing Breast-Conserving Surgery with Radical Mastectomy for Early Breast Cancer. N Engl J Med 2002; 347:1227-1232.
25. Wengstrom Y, Haggmark C, Strander H, Forsberg C. Perceived symptoms and quality of life in women with breast cancer receiving radiation therapy. Eur J Oncol Nurs. 2000; 4:78-88.
26. Wright J L et al, Prospective evaluation of radiation-induced skin toxicity in a race/ethnically diverse breast cancer population. Cancer Medicine 2016; 5 (3):454-464
27. Varga Z, Hideghéty K, Mezo T, Nikolényi A, Thurzó L, Kahán Z. Individual Positioning: A Comparative Study of Adjuvant Breast Radiotherapy in the Prone Versus Supine Position. Int J Radiat Oncol Biol Phys. 2009; 75 (1):94-100.

There is a need for apparatus and methods which can be used in conjunction with radiation treatment to reduce some of the above-noted problems. Because these problems are global, such apparatus would advantageously be reusable and economical to manufacture. Apparatus and methods that are effective to reduce the severity of skin reactions in women receiving whole breast radiation treatment should both improve the quality of life and reduce the adverse impact of radiation side effects for radiotherapy patients.

SUMMARY

The present invention has various aspects. These aspects provide apparatus and methods relating to support of the breast during treatment with radiotherapy.

One aspect of the invention provides apparatus for supporting a breast for radiation treatment. The apparatus comprises a paddle and a support structure. The paddle comprises first and second generally planar faces oriented at a right angle to one another. One face may be brought to bear against a lateral side of the breast. The other face may be brought to bear against an inferior side of the breast. The support provided by the first and second faces may reduce or eliminate skin folds on the lateral and inferior sides of the breast. The support structure is connected to hold the paddle at a desired position and orientation. The support structure is adjustable to bring the first face against and supporting the inferior side of a patient's breast while the second face is against and supporting the lateral side of the patient's breast.

In preferred embodiments the paddle is substantially transparent to radiation of the type to be used in the radiation treatment. In some embodiments the paddle and support structure are both substantially transparent to radiation of the type to be used in the radiation treatment. For example, the paddle and support structure may each comprise a carbon fibre composite material.

In some embodiments the support structure comprises a hoop that is attachable to a support board, wings to be used with a support board or a table of a radiation source such as a linear accelerator. The paddle may be coupled to the hoop by an adjustable arm assembly that allows adjustment of position and orientation of the paddle.

Another aspect of the invention provides a method for preparing a patient to receive radiation treatment. The method comprises arranging the patient in a supine position on a support board. The support board is angled upwardly toward the patient's head. For example, the support board may support the patient at an angle in the range of 9 to 16 degrees to horizontal. 12½ degrees to horizontal is an example angle for the support board. The method further comprises placing a paddle comprising first and second generally planar faces oriented at a right angle to one another against the patient's breast such that the first face of the paddle supports a lateral side of the patient's breast and the second face of the paddle supports an inferior side of the patient's breast.

Another aspect of the invention provides a method of medical treatment which involves supporting a patient's breast using any embodiment of the apparatus described herein and, while supporting the patient's breast delivering radiation to the patient's breast. In some embodiments the radiation is delivered perpendicular to a face of a paddle supporting the breast. In some embodiments the breast is supported such that there are no skin folds in the path of the radiation beam.

Another aspect of the present invention provides support of the breast with the radiotherapy patient in the supine position. A device for example as described herein provides support to the breast and reduces contact between mobile breast tissue and torso for pendulous breasts up to several litres in volume. The device provides support resulting in an improved breast position that will minimize skin folds as well as reducing the irradiated volume of heart, lung and liver, reducing the side effects of treatment. The curvature, size and setup position of the device accommodate the full range of breast sizes and shapes encountered in clinical practice.

In a further embodiment of the present invention, the apparatus may include breast supports designed to be specific to the left and the right breasts. In an alternative embodiment, a breast support adaptable to use for both the left and right breast may be provided.

In a some embodiments, imbedded radiopaque markers are provided that allow the device position to be visualized in x-ray images to ensure reproducibility. Further alternative embodiments include markers visible under infra-red or visible light, or markers consisting of electromagnetic transponders.

The curvature, size and setup position of the device may accommodate the full range of breast sizes and shapes encountered in clinical practice.

Further aspects and example embodiments are illustrated in the accompanying drawings and/or described in the following description.

BRIEF DESCRIPTION OF THE DRAWINGS

The accompanying drawings illustrate non-limiting example embodiments of the invention.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
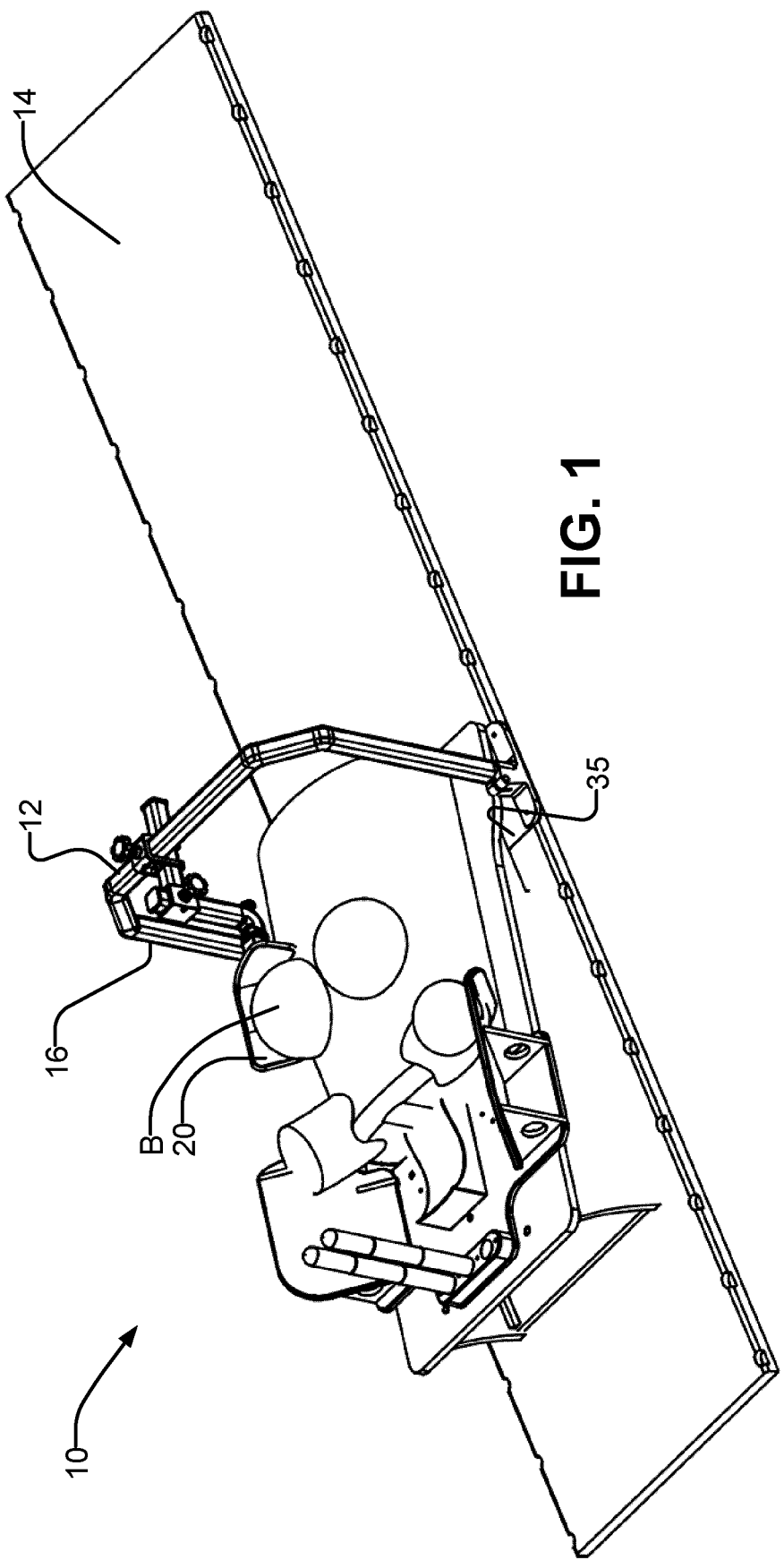
FIG. 1 is a perspective view of a breast positioning device according to an example embodiment with a schematic torso indicating a possible posture of a patient.

FIG. 1 shows a breast positioning device 10 according to an example embodiment. Breast positioning device 10 comprises a paddle 20 that supports a patient's breast. Paddle 20 is held at a desired location and orientation by an adjustable support structure 12.

Paddle 20 has first and second faces 20A, 20B that are oriented at approximately right angles to one another. In some embodiments faces 20A and 20B are generally flat (planar). In some embodiments faces 20A and 20B are connected by a curved corner portion 20C (see FIG. 10 for example). In some example embodiments curved corner portion 20C has a radius of curvature in the range of about 30 mm to 70 mm. In an example embodiment, curved corner portion 20C has a radius of curvature of 50 mm. Paddle 20 may be described as having a scoop shape or being like a scoop.

Paddle 20 has a height (i.e. distance between a top edge and a bottom edge of first and second faces 20A, 20B) sufficient to provide support to breast tissue that will reduce or eliminate skin folds. In some embodiments the height is in the range of about 5 cm to about 15 cm. In some embodiments the height is in the range of about 6 cm to about 10 cm. In an example embodiment, paddle 20 has a height of 8 cm.

Figure 10:
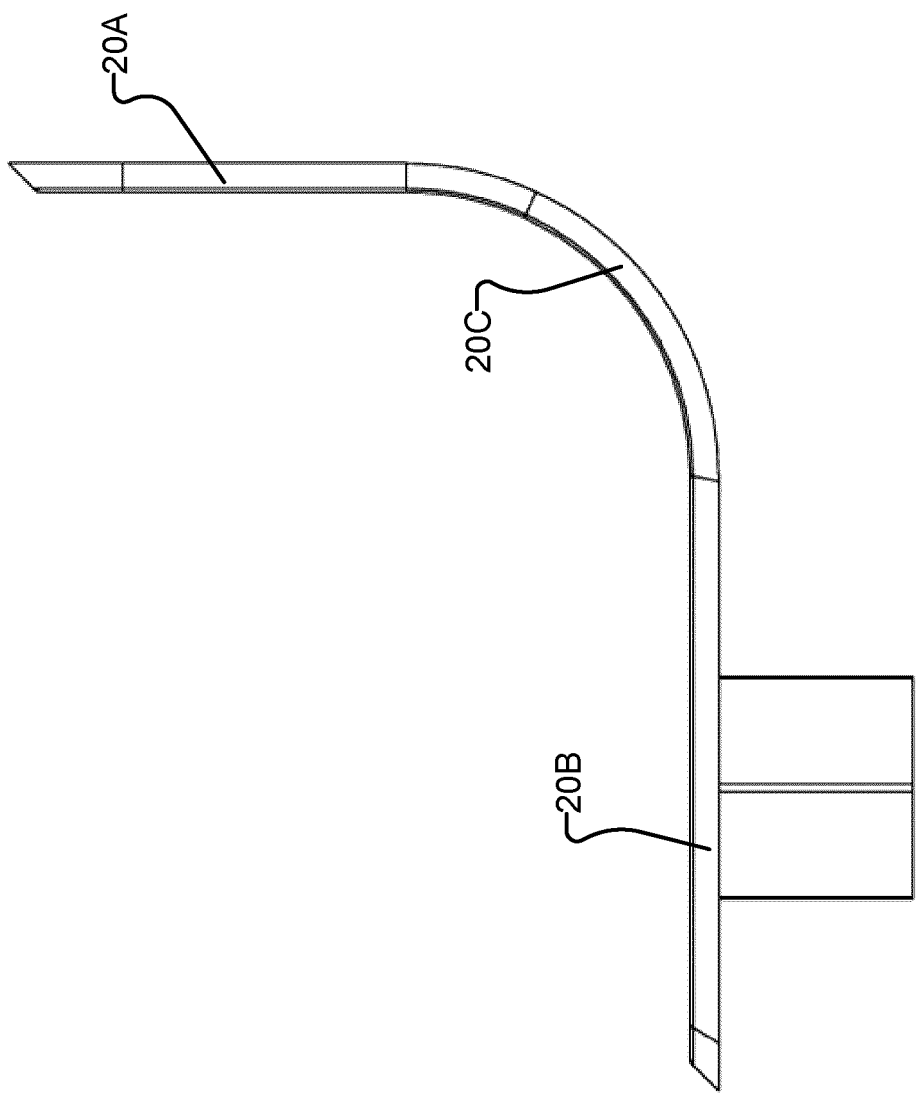
FIG. 10 is a top view of a paddle for breast support, according to an example embodiment.

The first and second faces 20A and 20B have widths sufficient to provide a desired area of support to a breast. In some example embodiments, first face 20A and second face 20B have widths in the range of 10 to 20 cm. In some embodiments first face 20A (normally used to support a lateral outside of a breast) is narrower than second face 20B (normally used to support a bottom—i.e. inferior—side of the breast). FIG. 10 shows an example of this construction. In some embodiments a distance from an outside edge of first face 20A to the plane of second face 20B is in the range of about 10 cm to about 15 cm (for example, 12 cm in an example embodiment). In some embodiments a distance from an outside edge of second face 20B to the plane of first face 20A is in the range of about 11 cm to about 16 cm (for example, 13½ cm in an example embodiment).

As mentioned in the Background section above, it can be desirable to deliver a whole breast radiation treatment when a patient is lying in a supine position on an angled support board (also known as a 'breast board'). FIG. 1 shows a support board 14. Support board 14 may be tilted at a suitable angle to horizontal. For example, support board 14 may have an angle in the range of 9 to 15 degrees to horizontal (other angles may also be used). In an example embodiment, the top surface of support board 14 is inclined at an angle of 12.5 degrees to horizontal. Apparatus 10 may advantageously be designed to accommodate use of various commercially available support boards.

Radiation is typically delivered to one breast at a time. Support board 14 supports the patient with her head raised relative to her waist. In this position her breast to be treated will tend to fall toward her abdomen and/or laterally toward the axilla.

Figure 2:
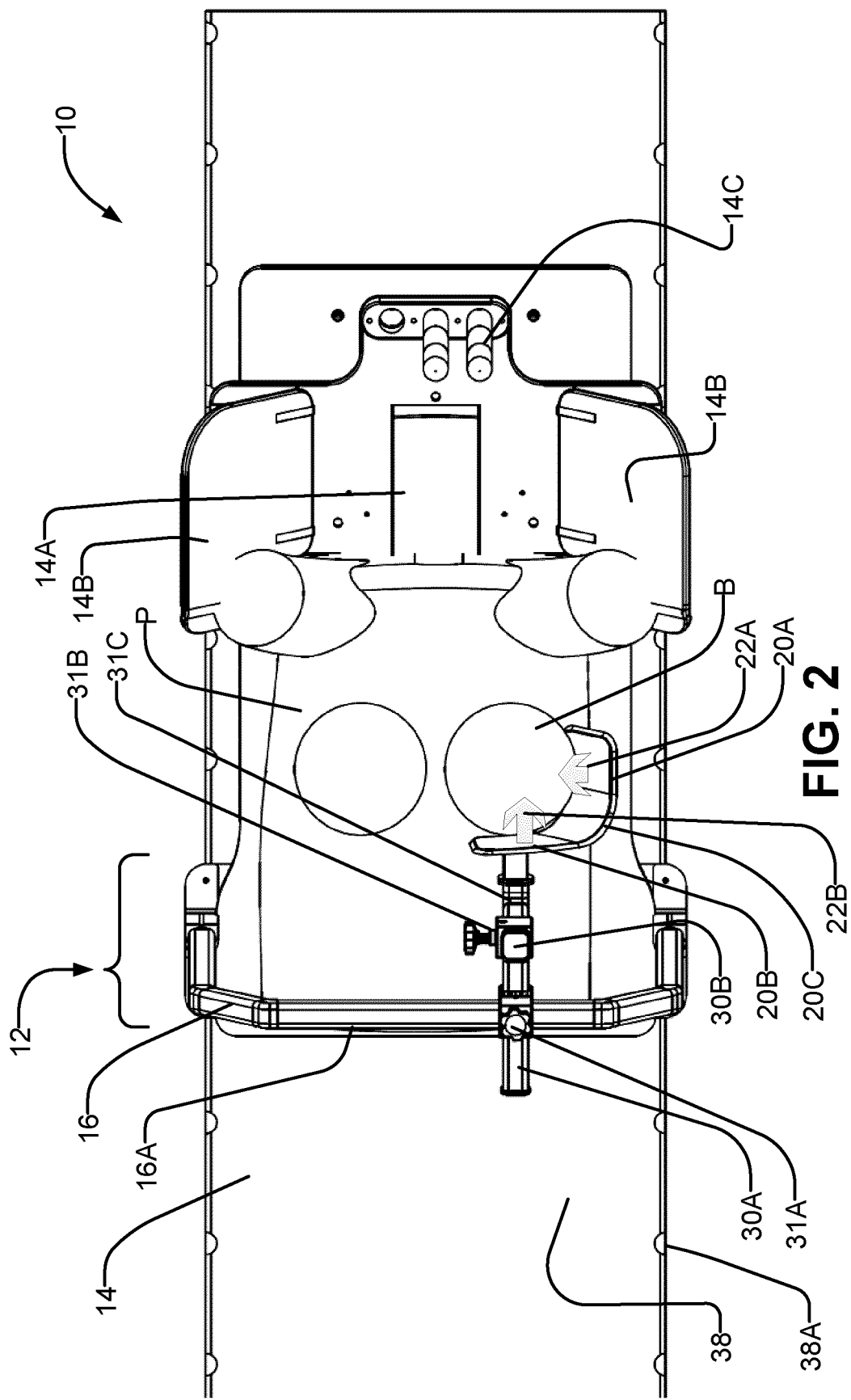
FIG. 2 is a top plan view of the apparatus shown in FIG. 1.

As shown in FIG. 2, paddle 20 may be placed against a breast B so that face 20A holds breast B from falling laterally as indicated by arrow 22A and face 20B holds breast B from falling toward the patient's abdomen as indicated by arrow 22B.

Paddle 20 may be configured so that the lower edge of face 20B is shaped with curves that follow the curve of the patient's body laterally across the chest. Lower edge of face 20A may be shaped to follow the patient's body in the superior-inferior direction. For example, the lower edge may extend at an angle in the range of a few degrees (e.g. about 8° to about 15° below horizontal) as face 20A extends away from curved portion 20C. In an example embodiment, the lower edge of face 20A or an outside portion of the lower edge of face 20A extends at an angle of 12° below horizontal.

It is desirable for paddle 20 to fit snugly against the skin of the patient's torso along the infra-mammary and lateral breast-chest wall. To facilitate such fitting, in some embodiments the lower edge of face 20B may be gently concave. For example, the lower edge of face 20B may have a radius of curvature in the range of about 150 mm to about 300 mm, for example, in order to approximate the curvature of a patient's torso and chest. In an example embodiment, the lower edge of face 20B has a radius of curvature of 170 mm. In another example embodiment, the lower edge of face 20B has a radius of curvature of 250 mm.

Figure 1A:
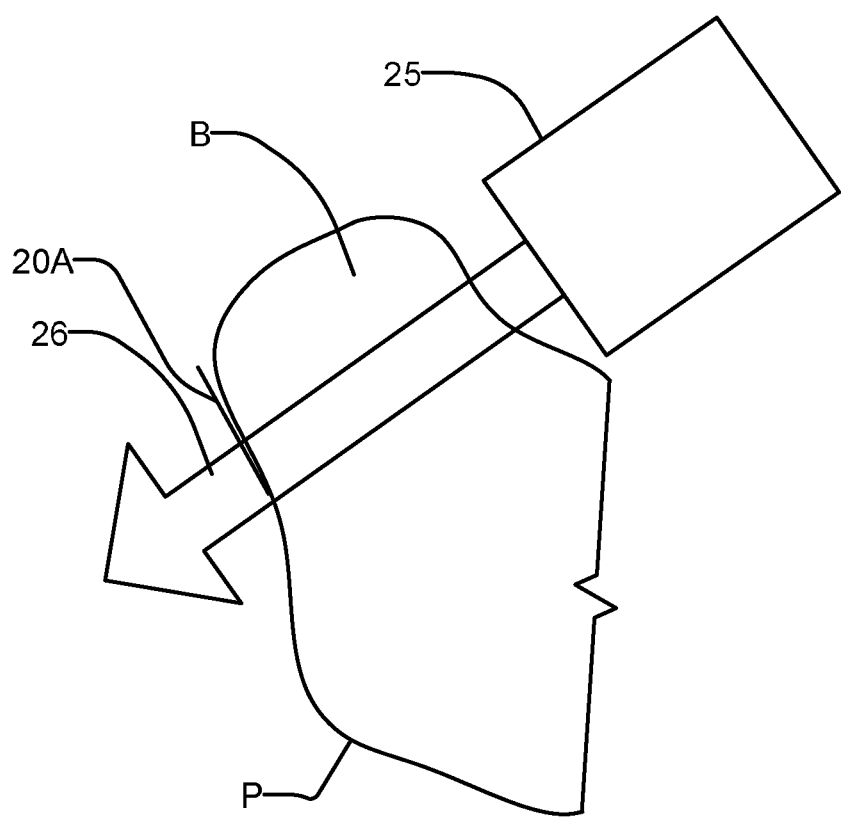
FIGS. 1A and 1B are schematic illustrations showing delivery of radiation to a supported breast using medially and laterally-directed radiation beams.
Figure 1B:
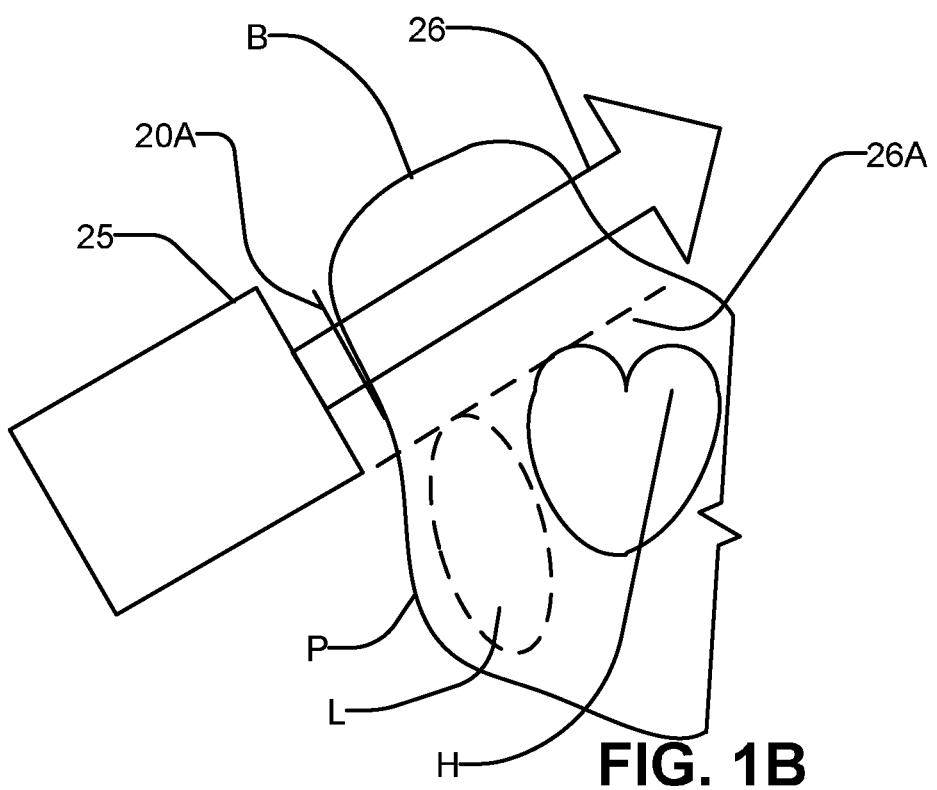

FIGS. 1A and 1B schematically illustrate a configuration for delivering radiation treatment to a patient's left breast B. A radiation source 25 (e.g. a head of a linear accelerator) emits a beam 26 of radiation. In order to achieve a relatively uniform dose radiation is delivered in two directions through the patient's breast B (for example as indicated schematically in FIGS. 1A and 1B)

Figure 1C:
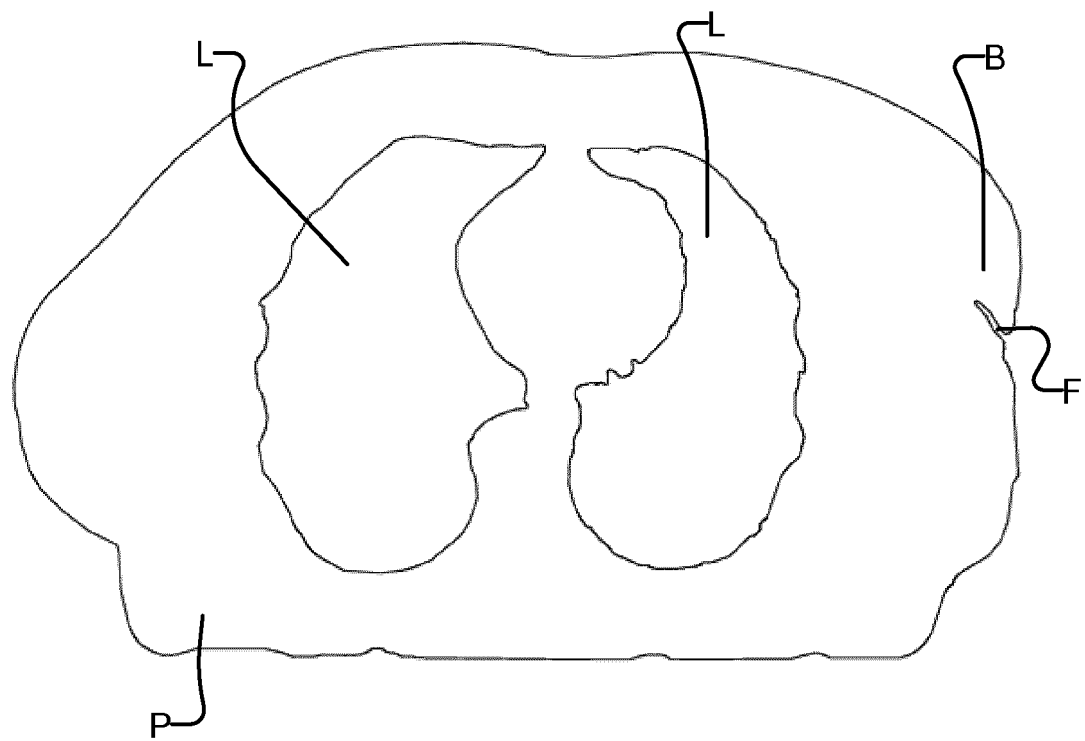
FIGS. 1C and 1D are top views of a patient respectively without and with support from a breast positioning device according to one embodiment of the invention.
Figure 1D:
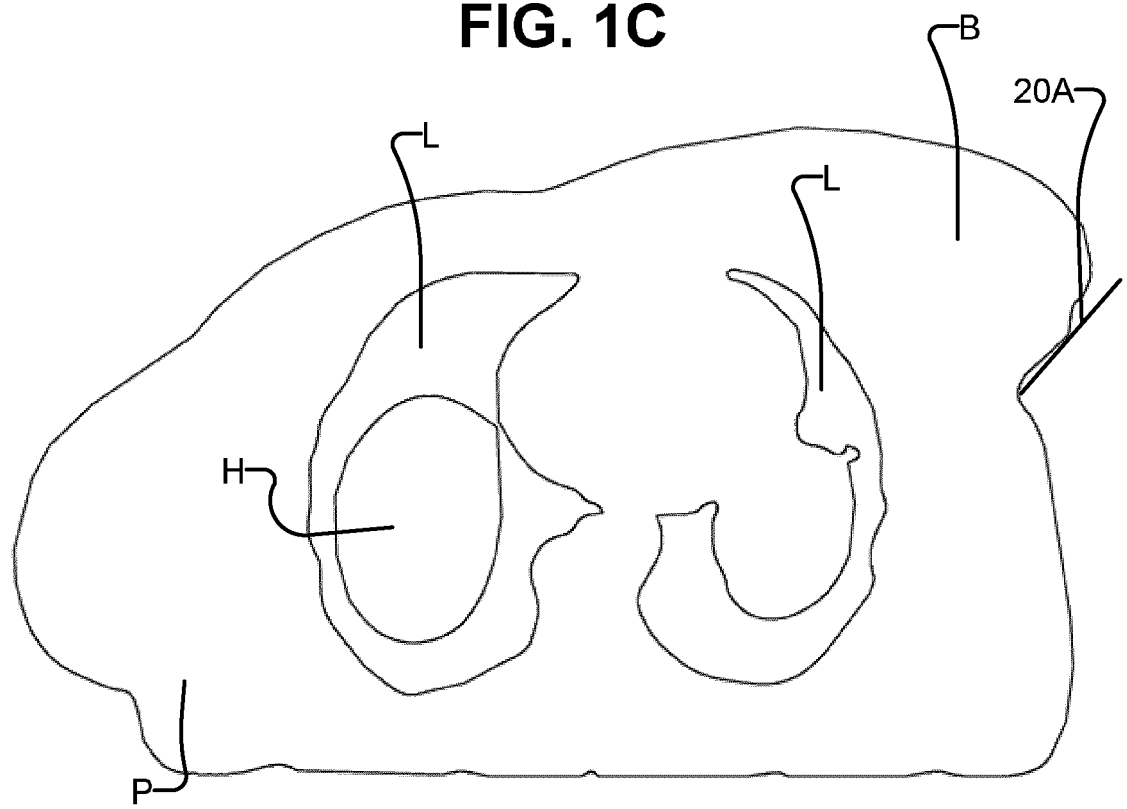
Figure 1E:
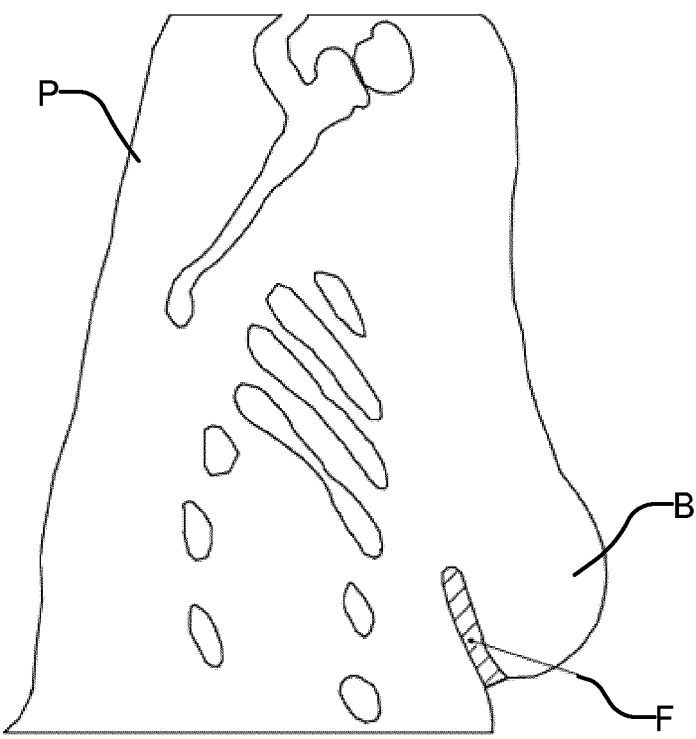
FIGS. 1E and 1F are respectively side views of the patient shown in FIGS. 1C and 1D without and with support from the breast positioning device.
Figure 1F:
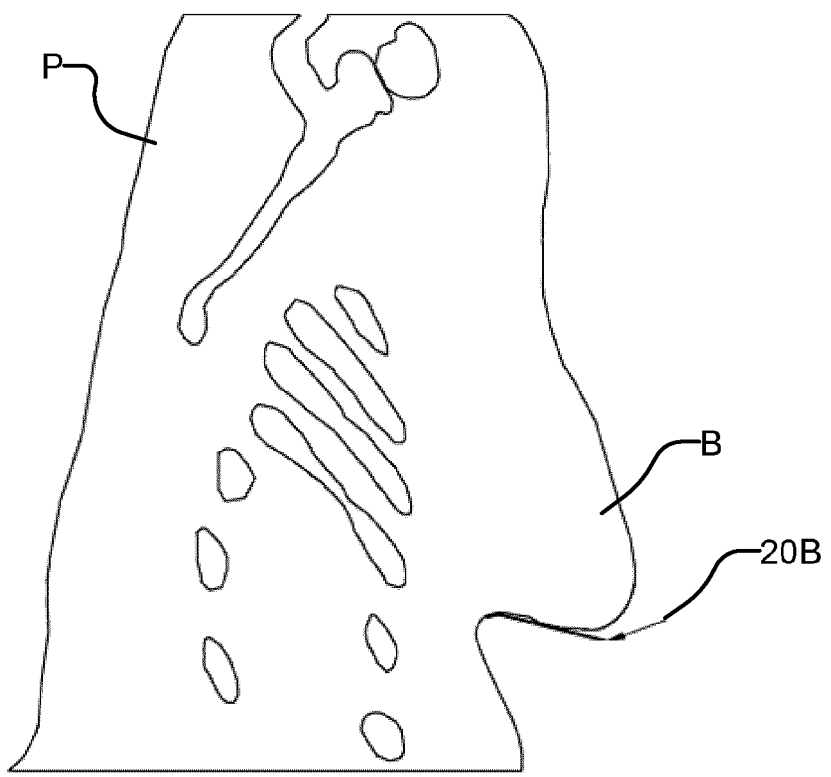

Paddle 20 holds breast B in position during delivery of the radiation. The breast tissue is supported against faces 20A and 20B (face 20B is shown in FIGS. 1E and 1F) so that the skin of breast B does not form folds. FIGS. 1C and 1E illustrate a skin fold F on the outside of the patient's right breast. As shown in FIGS. 1D and 1F, skin fold F may be at least substantially eliminated when breast B is supported by paddle 20. Preferably paddle 20 is oriented so that face 20A (and the skin in contact with face 20A) is perpendicular to radiation beam 26.

As shown in FIG. 1B, by supporting the tissue of the breast B being irradiated outward from the chest wall, radiation beam 26 can be directed to irradiate all of the tissue of breast B while minimizing radiation dose delivered to the patient's heart H and lungs L. In particular, supporting breast B using paddle 20 may allow radiation field borders 26A to be moved in superior and/or medial directions (as compared to where field borders would be placed in the absence of paddle 20) while preserving desired margins around the breast tissue. Supporting breast B using paddle 20 may configure breast B so that the location of breast tissue is better defined. This may allow margins around breast tissue to be reduced while preserving confidence that all breast tissue of breast B is being irradiated.

In some embodiments, left breast patients are treated using the deep inspiration breath hold (DIBH) technique in order to reduce dose to the heart and lung.

To receive treatment a patient P may lie on support board 14 in a supine position as illustrated in FIG. 2 with her head on a headrest 14A. She may rest her elbows on wing boards 14B and hold handgrips 14C. Paddle 20 may be positioned as described herein to support the breast to which radiation treatment will be delivered.

Advantageously, paddle 20 may accommodate breasts of many different sizes and configurations. It is not necessary for paddle 20 to be custom formed to fit any individual patient's breast.

Figure 9:
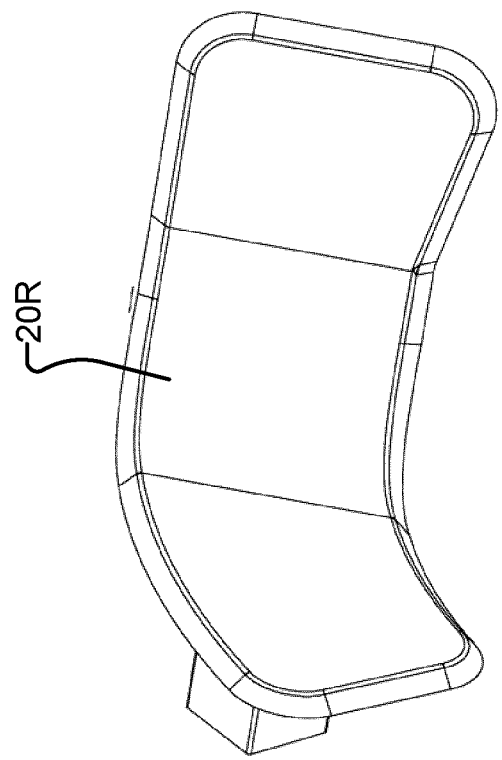
FIG. 9 is a perspective view of a set comprising left and right paddles for breast support according to an example embodiment.
Figure 9:
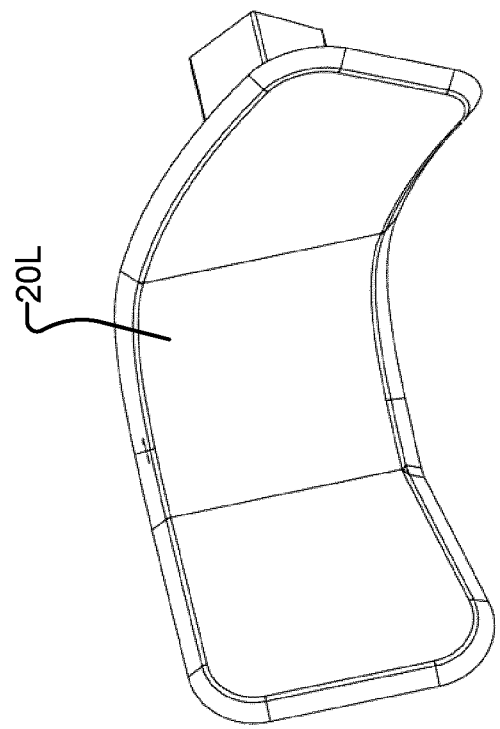

Optionally paddle 20 is detachably coupled to arm 12. Mirror image paddles 20 may be provided for supporting left and right breasts of a patient. For example, FIG. 9 shows a set containing paddles 20L and 20R for supporting left and right breasts respectively. The paddles may be interchangeably mounted to arm 12. Optionally paddles 20 of different sizes may be provided. Different sizes of paddles, if provided, may be interchangeably mounted to support structure 12.

Paddle 20 is preferably made of a material that is substantially transparent to radiation of the type used in the radiation treatment. Materials made of elements that have low atomic numbers tend to be relatively transparent to radiation. Carbon fibre is a good material for making paddle 20 because it is quite transparent to radiation, a thin layer of carbon fibre can be quite stiff, the surface of a carbon fibre composite material can be made smooth and readily cleanable and carbon fibre composites can be readily formed to have desired shapes such as the shape of paddle 20. Foam materials such as reasonably stiff closed cell foams are another non-limiting example of materials that may be used to provide paddle 20.

For high energy radiation beams (e.g. MeV beams), the dose delivered to skin covered by a support will typically be larger than the dose delivered to bare skin under the same conditions. This is at least in part because the high energy beam will scatter electrons from the material of support and the scattered electrons will deposit dose in the skin. This effect may be minimized by making the support more transparent to the radiation beam. In the case of paddle 20 this may be achieved through a combination of making face 20A (or both faces 20A and 20B) to be:
 thinner;
 formed with apertures, voids and/or reduced thickness areas; and/or
 formed from materials that have a reduced tendency to scatter photons from the radiation beam.

Figure 7:
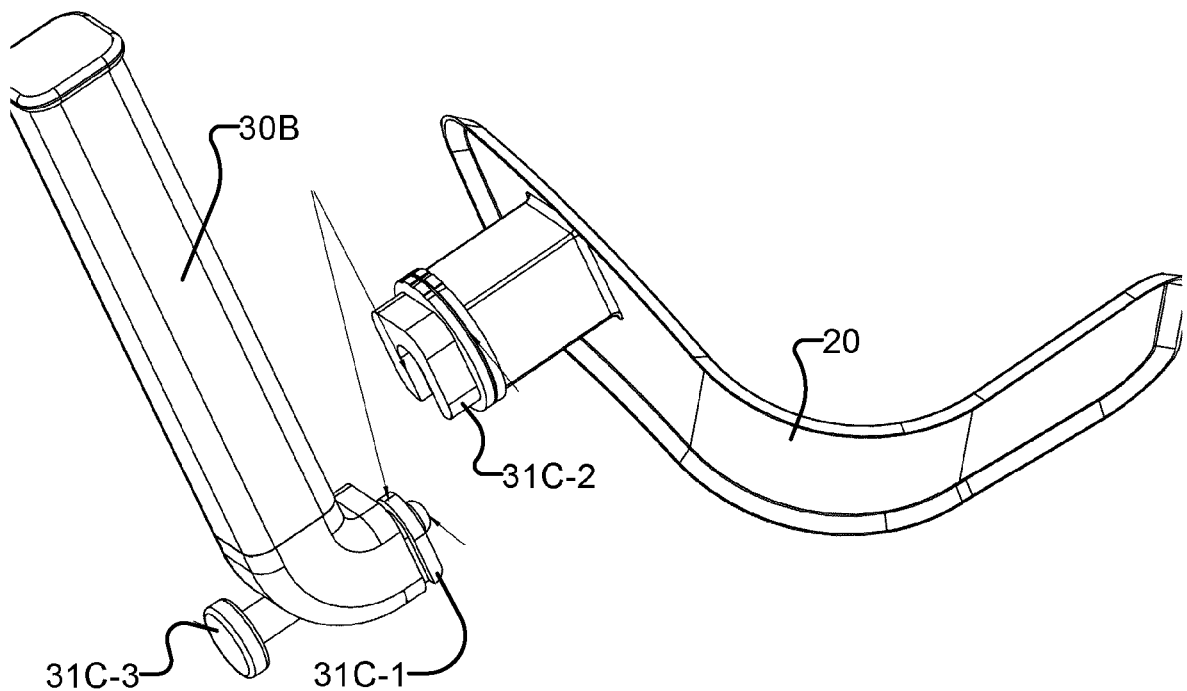
FIG. 7 is an enlarged perspective view of an example coupling for coupling a paddle to a support arm assembly.

As shown, for example, in FIG. 7, a paddle 20 may be formed of a thin layer of carbon fibre or another suitable material. Peripheral edges of paddle 20 may be folded back so that sharp edges are not presented to the patient's skin.

Figure 3A:
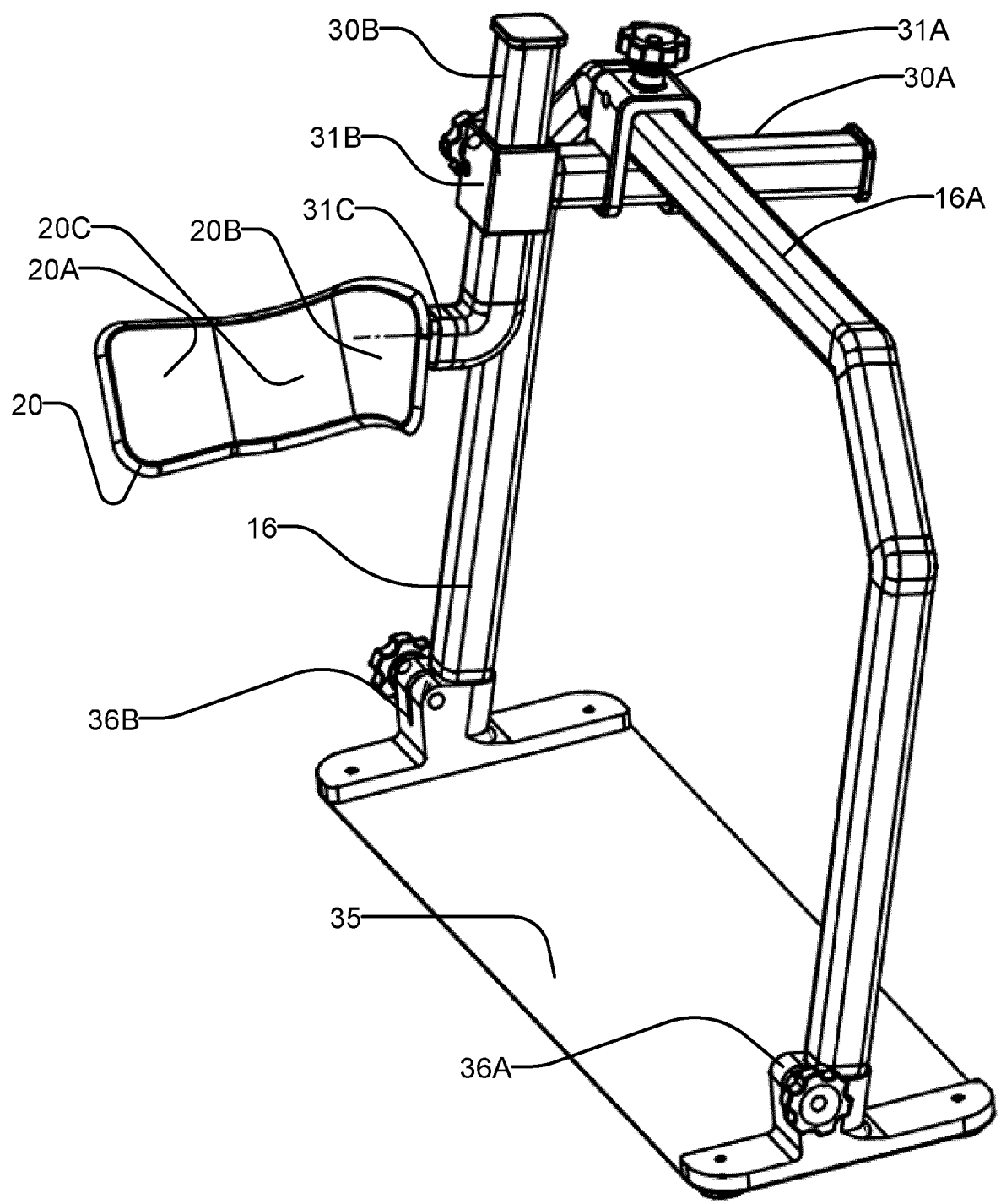
FIGS. 3A and 3B are respectively a front perspective view and a rear perspective view of a breast support according to an example embodiment.
Figure 3B:
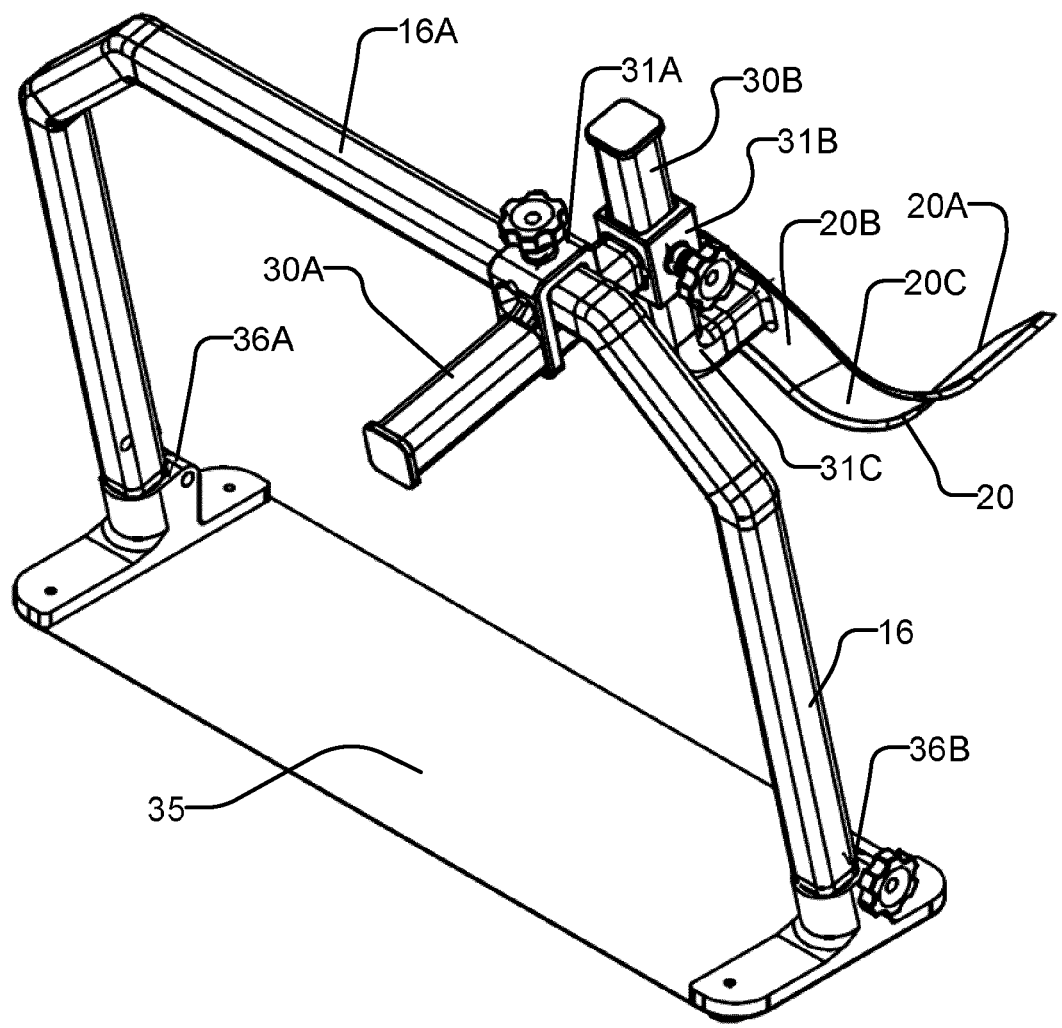
Figure 4:
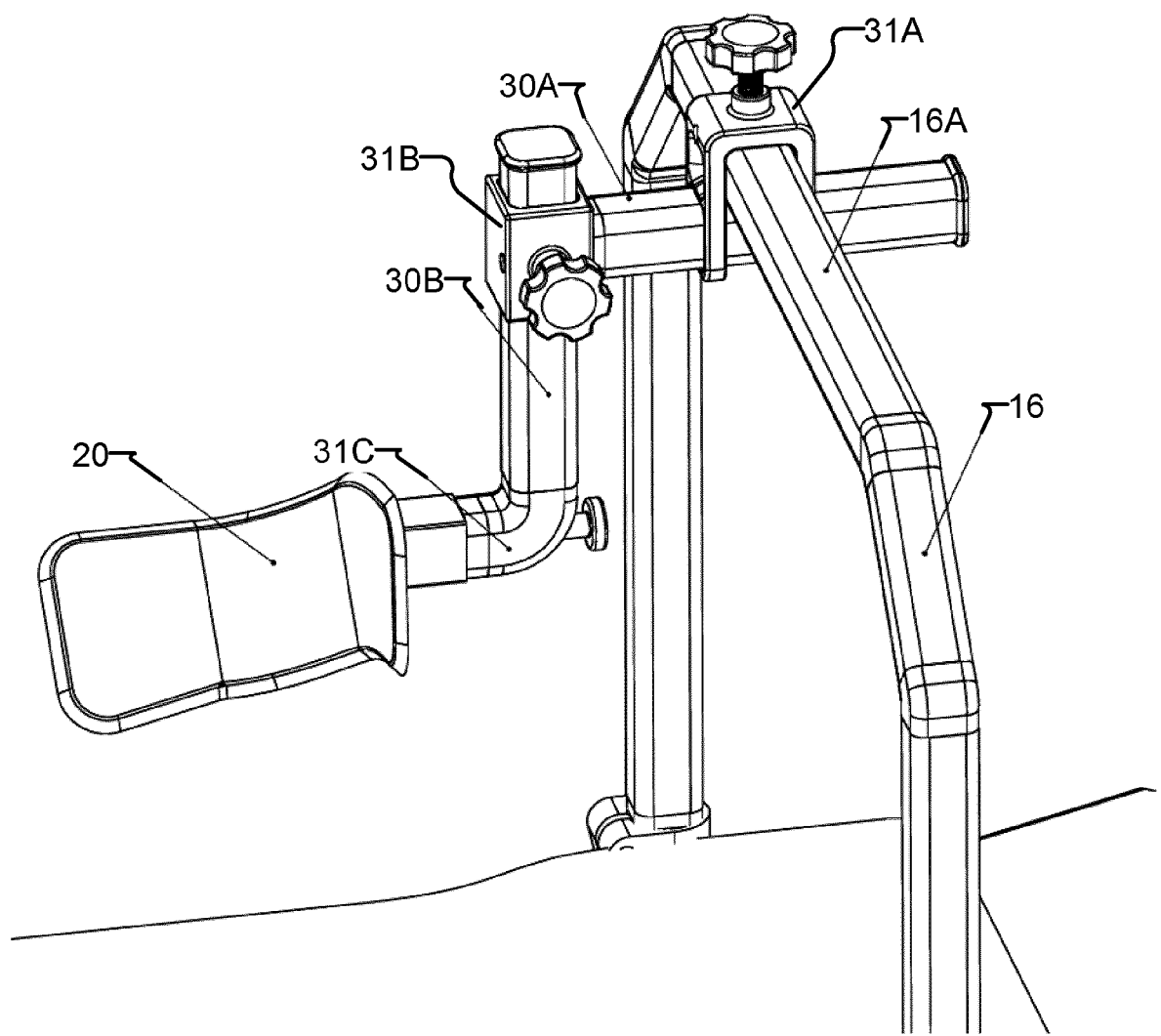
FIG. 4 is an enlarged view of the apparatus of FIGS. 3A and 3B showing a paddle and support arm.

In some embodiments, as shown, for example in FIGS. 3A and 3B, support structure 12 comprises a hoop or arch 16 that extends over support board 14. The part of hoop 16 that passes over support board 14 is high enough to pass over the largest anticipated patients. In some embodiments hoop 16 is positioned to pass over the lower torso or waist of a patient.

Hoop 16 provides a rigid base for an adjustable arm assembly 30 that supports paddle 20. In some embodiments a central part 16A of hoop 16 is straight and horizontal. In some embodiments central part 16A extends in a transverse direction at right angles to a centerline of support board 14.

Hoop 16 may be made wide enough and high enough to accommodate any of a wide variety of commercially available or custom made breast boards.

Various constructions are possible for arm assembly 30. The function of arm assembly 30 is to firmly support paddle(s) 20 in appropriate positions for delivering radiation to a patient's breasts while allowing proper positioning of radiation source 25. The illustrated arm assembly 30 comprises a first arm 30A that is coupled to hoop 16 by a clamp 31A. First arm 30A extends perpendicular to hoop 16. Clamp 31A can be released to allow first arm to be moved transversely (back and forth along hoop 16) as well as in an inferior/superior direction (longitudinally of first arm 30A and at right angles to hoop 16). Clamp 31A can be locked to hold arm 30A in a set position relative to hoop 16.

A second arm 30B is coupled to first arm 30A by a clamp 31B. Clamp 31B can be released to allow arm 30B to be moved vertically (longitudinally of arm 30B and at right angles to central part 16A of hoop 16 and to arm 30A). Clamp 31B can be locked to hold arm 30B in a set position relative to arm 30A.

Paddle 20 is coupled to a lower end of arm 30B by a coupling 31C. Coupling 31C can be released to allow paddle 20 to be rotated about an axis 31D that is at generally at right angles to arm 30B. Coupling 31C can be locked to hold paddle 20 at a desired angle of rotation around axis 31D. As shown, for example, in FIG. 7, coupling 31C may be constructed to permit detachment of paddle 20. Coupling 31C comprises a part 31C-1 carried by arm 30B that is configured to mate with a part 31C-2 carried by paddle 20. For example, as shown in the embodiment of FIG. 7, part 31C-2 may comprise a groove which mates with a corresponding tongue on part 31C-1. A knob 31C-3 is provided to release coupling 31C. Other configurations of parts 31C-1 and 31C-2 are possible. Provision of a detachable coupling 31C facilitates use of interchangeable paddles 20.

A set of paddles 20 may include one or more pairs of paddles 20 with the paddles 20 in each pair configured for supporting left and right breasts respectively. Different pairs may be configured for breasts of different sizes. In paddles 20 configured for larger breasts, faces 20A and 20B may be larger in one or both of a first direction parallel to an axis of curvature of corner part 20C and a second direction perpendicular to the first direction.

Figure 6:
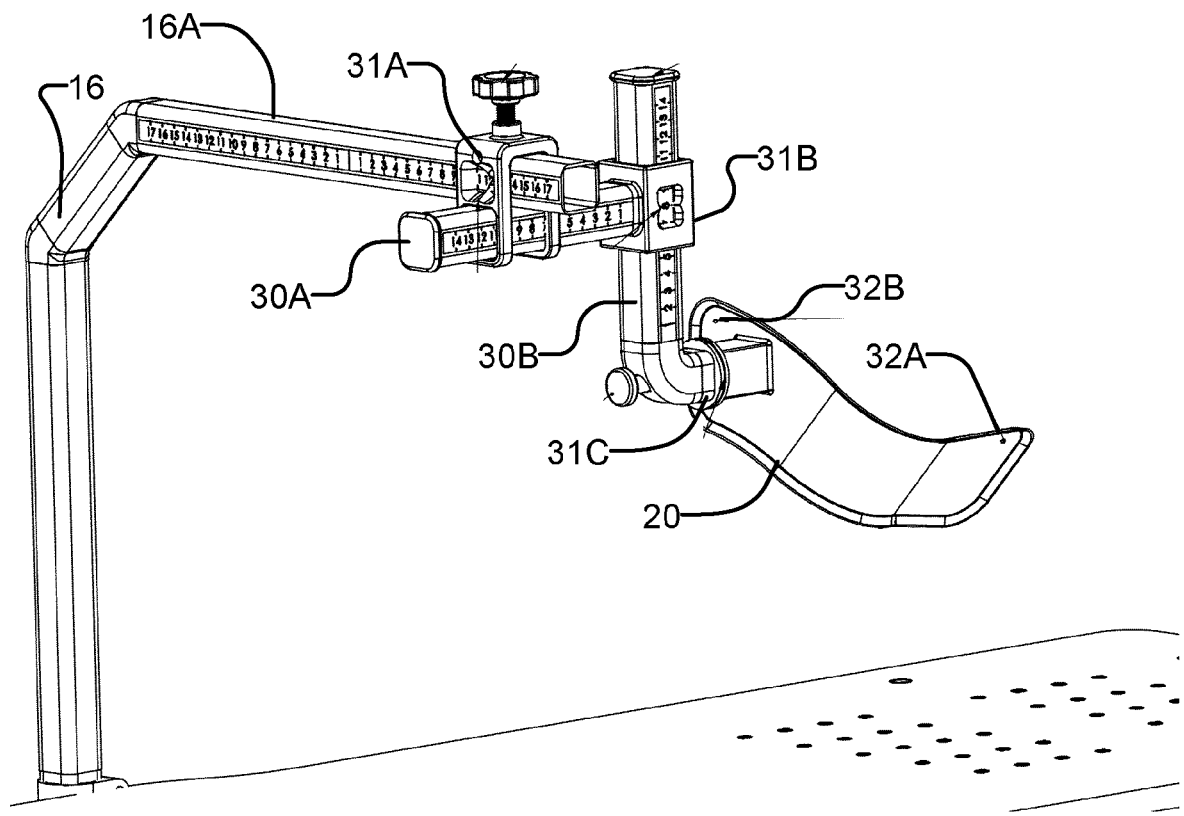
FIG. 6 is an enlarged perspective view showing example measurements for indicating positions of components of a support arm assembly and indicia for aligning the apparatus to a patient.

As illustrated in FIG. 6, indicia may be marked along part 16A of hoop 16, arm 30A and/or arm 30B. Such indicia may be used to repeatably place arms 30A and 30B into a desired configuration. This may be useful, for example, to set up apparatus 10 for delivery of radiation treatments to a specific patient in spaced apart sessions. The indicia may comprise, for example, numbers marked at set distances (for example, every centimetre) along part 16A, arm 30A, and/or arm 30B. Clamps 31A and 31B may comprise indicators (e.g. arrows or windows) or the like for identifying the indicia and the relative positions of part 16A, arm 30A, and arm 30B.

In some embodiments paddle 20 comprises indicia that may be aligned with fiducial marks (e.g. tattoo spots) on a patient to repeatably align paddle 20 to the patient. FIG. 6 shows example indicia 32A and 32B. These indicia may, for example, comprise small apertures in paddle 20.

Figure 5:
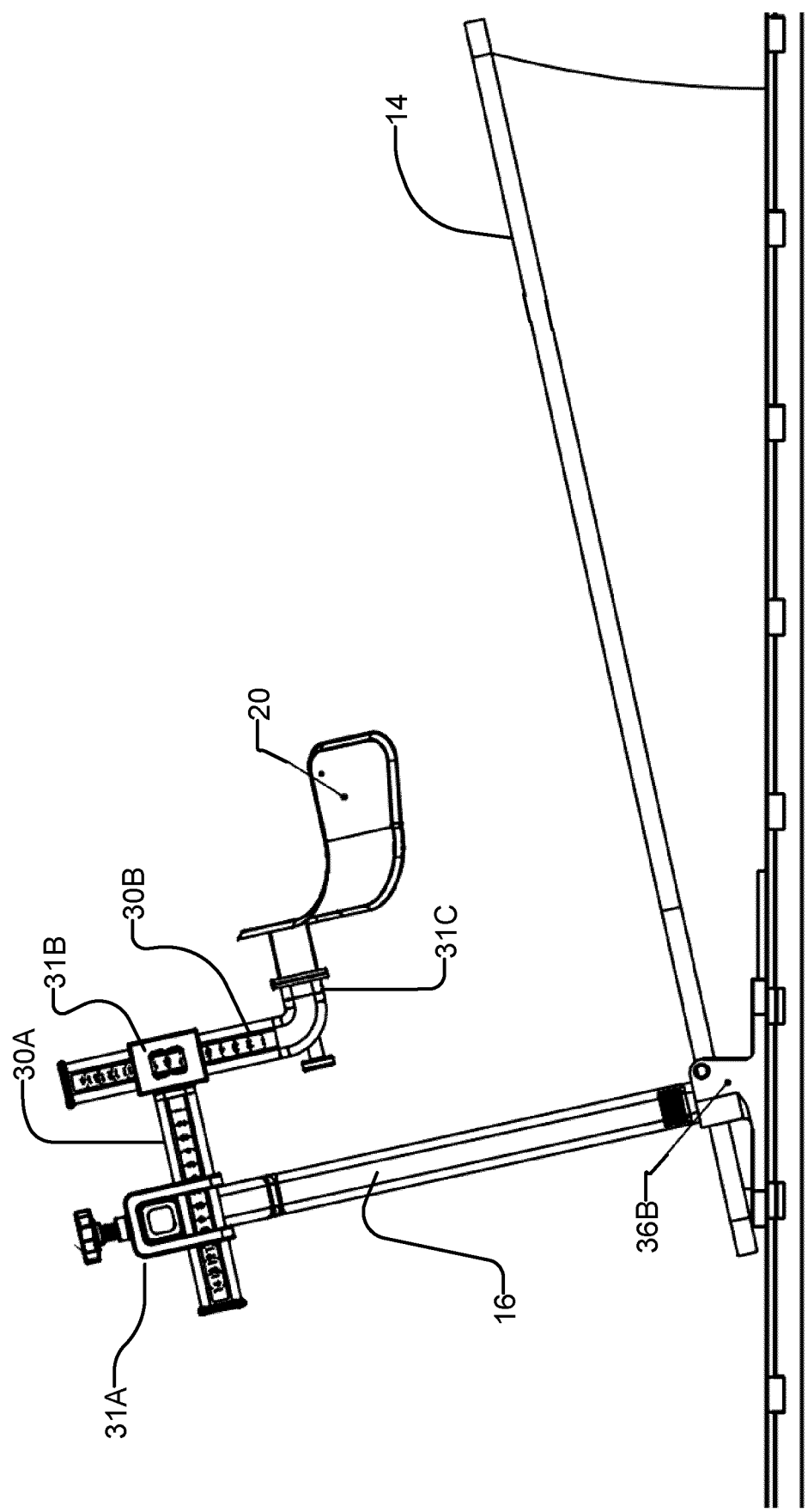
FIG. 5 is a side elevation of the apparatus of FIGS. 3A and 3B on a table of a radiation source with an angled support board.

Conveniently, in the illustrated embodiment, part 16A of hoop 16, arm 30A and arm 30B are mutually perpendicular. Thus measurements of the positions of arm 30A along part 16A of hoop 16, the longitudinal position of arm 30A and the longitudinal position or arm 30B can be interpreted as coordinates in a rectilinear coordinate system. As shown best in FIG. 5 arm assembly 30 may be oriented with arm 30A parallel to support board 14 such that available movements of arm 30A are in a plane parallel to support board 14 and available movements of arm 30B are perpendicular to the surface of support board 14.

Figure 8:
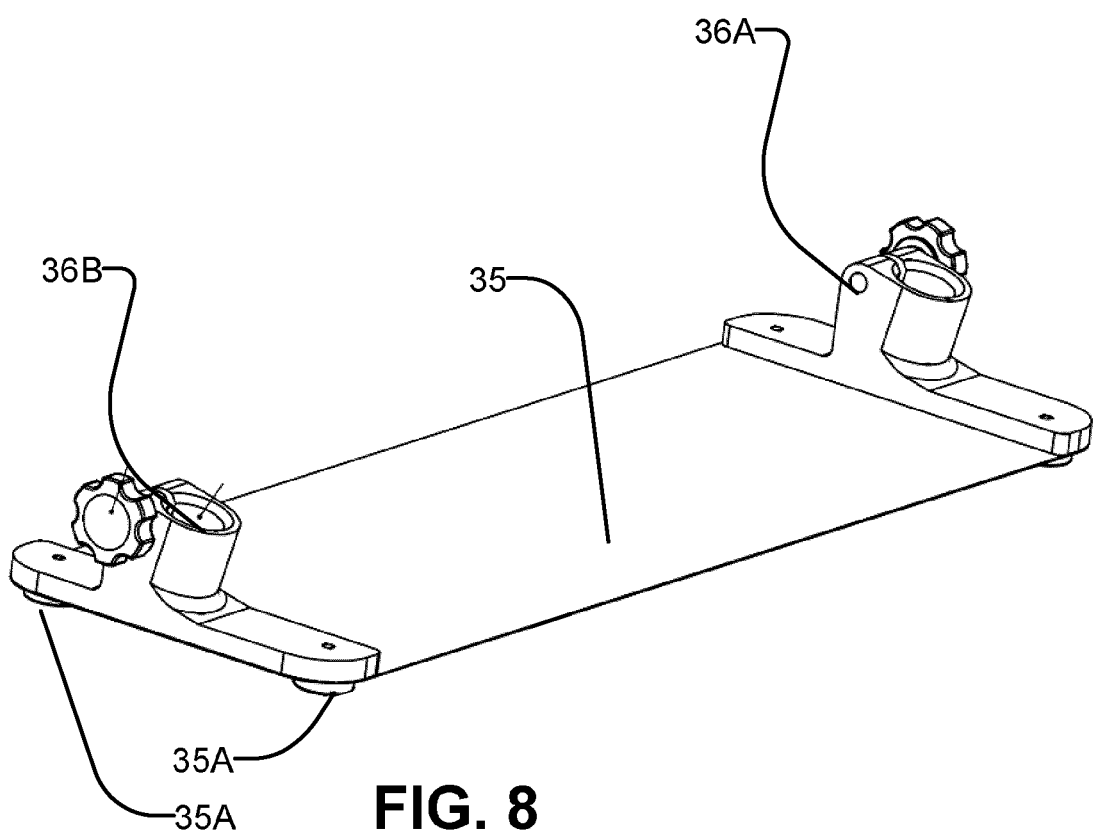
FIG. 8 is perspective view of an example base for a support structure that may be attached to a table of a radiation source.

As shown in FIG. 8, support structure 12 may be adapted to be removably attached to a table of a radiation delivery device such as a linear accelerator. FIG. 8 shows a thin mounting plate 35 to which are mounted clamps 36A and 36B. Mounting plate 35 may be affixed to a table of a radiation delivery machine using suitable fasteners (not shown). A support board 14 may be placed over mounting plate 35. Opposing ends of hoop 16 may then be engaged with and held in place by clamps 36A and 36B respectively.

Patient support tables or 'couches' in many commercially available radiation sources include registration features which allow accessory equipment to be repeatably placed at specific locations on the couches. One common type of registration feature is provided by indexing indentations arranged along opposing edges of the couch. The indexing indentations may be spaced apart along the couch at regular intervals. Accessory equipment may comprise projections that engage the indexing indentations. For example, where the indexing indentations are arcuate the accessory equipment may comprise cylindrical pucks that can engage corresponding indexing indentations.

FIG. 2 illustrates an example case where couch 38 provides indexing indentations 38A spaced apart along opposing edges of the couch. Mounting plate 35 may have attached pucks 35A (see FIG. 8) that are properly spaced apart and dimensioned to engage indexing indentations 38A.

Mounting plate 35 is advantageously formed, for example, of a suitable carbon fibre composite or plastic.

In some embodiments (see e.g. FIG. 5) clamps 36A and 36B are angled so that end parts of hoop 16 are oriented generally perpendicular to a support board 14. For example, clamps 36A and 36B may be oriented to receive ends of hoop 16 that are at an angle of 9 to 16 degrees from vertical.

Support structure 12 is preferably itself transparent to radiation or nearly so. For example, hoop 16, arm 30A and/or arm 30B may be made of a carbon fiber composite material. For example these parts may be made of carbon-fibre fabric pre-impregnated with resin. An example commercially available resin is Prepreg 3K available from Fibre Glast Developments Corp, www.fibreglast.com of Ohio USA. Such composite materials may be formed for example using an aluminum mold and cured by means of heat to produce robust accessories.

Clamp 31A, clamp 31B, coupling 31C, clamp 36A and/or clamp 36B may be made, for example, of suitable plastic materials. In some embodiments support structure 12 or arm assembly 30 has no parts made of metal.

Advantageously, apparatus 10 may be dimensioned to fit within the bore of an imaging device such as a computed tomography (CT) scanner. This permits imaging for radiation treatment planning to be performed while a patient is in exactly the same position as she will be in when the radiation treatment is delivered. In some embodiments plural radiopaque markers are imbedded in or attached to support structure 12. Such markers may allow the configuration of apparatus 10 to be visualized in x-ray images.

In some embodiments markers are attached to apparatus 10 at known locations. The markers may be of types that can be located with computer vision systems, stereo camera systems or the like. The markers may comprise markers of a position sensing system that may be located in space using the position sensing system. Three or more markers may be attached to apparatus 10 such that the position and orientation of apparatus 10 in space may be determined from measured positions of the markers. Such markers may be applied together with a corresponding system configured to measure positions of the markers to check that apparatus 10 is configured in a desired way for a particular patient and/or to check that apparatus 10 has a desired location and orientation relative to a radiation source and/or to check that apparatus 10 has a desired location and orientation relative to fiducial features of a patient.

Making the entire apparatus 10 with no metal parts can be beneficial for allowing magnetic resonance imaging (MRI) of a patient being supported by apparatus 10. MRI may optionally be used to obtain images of the patient useful for planning radiation treatment.

Clamps 31A and 31B and 36A and 36B are illustrated as screw clamps. However, other clamping arrangements such as cams, wedges, resilient clamping members or the like could be provided in alternative constructions.

The illustrated support structure 12 is but one example of a support structure that could be used to support a paddle 20. While the illustrated support structure 12 has various advantages, alternative configurations of support structure 12 may be provided. In some embodiments a support structure 12 includes a support arm which attaches to an existing breast board or wing board patient positioning device. In some embodiments a support structure is mounted to a table of a radiation delivery device at a single point. In some embodiments plural separate support structures are provided. For example, one support structure may carry a paddle for supporting a patient's left breast and another support structure may carry a paddle for supporting the patient's right breast.

Apparatus as described herein may be applied, for example to support and reduce or eliminate folds in pendulous breasts up to several litres in volume. Use of the apparatus may provide an improved breast position which permits reduction in the irradiated volume of heart, lung and body tissues, thereby reducing the side effects of radiation treatment. The apparatus may be used, for example, in conjunction with delivering radiation treatments to patients with breast cancer or DCIS undergoing adjuvant radiotherapy following breast-conserving surgery. The apparatus may improve treatment outcomes while permitting radiation delivery with the patient in a supine position. Such apparatus has wide application in reducing breast sag and skin folds for women with large volume or pendulous breasts who are undergoing radiation therapy.

It can be appreciated that apparatus according to some embodiments have one or more of the following advantages:
- the apparatus may be used together with any of a wide range of radiation delivery systems;
- the apparatus may be used together with any of a wide variety of support boards; and/or
- the apparatus may be used with patients having body-types and breasts of a wide range of shapes and sizes.

EXAMPLE 1

One example embodiment of the present invention provides a curved carbon fibre support scoop mounted on a support arm which attaches to a breast board patient positioning device. The breast board patient positioning device may be of an existing type. Carbon fibre construction provides rigidity for support while maintaining transparency to radiation and will not significantly increase the dose to the skin. In addition, the device is designed to minimize discomfort to the patient and enhance reproducibility of patient setup. In alternative embodiments, other materials compatible with the delivery of radiotherapy treatment that maintain transparency to radiation may be selected.

Tests with a prototype version of the device described above found that the device fit all participants in the study and could be adjusted to visibly eliminate all inferior and lateral skin folds. Radiation therapists' experience when testing the device has been positive. The tested device prototype weighs 870 grams and can be set up in less than 1 minute.

Tests of an early prototype version of the carbon fibre breast support showed an increase in the entrance surface dose of 30-40% compared with bare skin surface. Surface dose is maximum at the inferior 90° position of the breast due to tangential beam incidence. Despite the increase in dose for the lateral beam due to presence of the carbon fibre "scoop", the total combined skin dose for a tangential pair of 6 MV beams with the support scoop in place was ≤80% of the prescribed target dose. This example represents the worst case scenario and improves with 10 MV beams and thinner construction of the scoop.

EXAMPLE 2

An aspect of the present invention provides a method and apparatus to reduce the dose absorbed in skin folds through better breast positioning. A prototype has been tested at the BC Cancer Agency in Vancouver, Canada. The standard BC Cancer Agency protocol for whole breast radiation therapy is the delivery of a tangent pair of high energy photon fields (with or without internal mammary, supraclavicular and/or axillary nodal fields). One beam enters the breast medially (see e.g. FIG. 1A) and the second beam enters the breast laterally (see e.g. FIG. 1B). The posterior field border is placed such that all of the breast tissue is encompassed.

As the breast tissue wraps around the chest wall, some lung, ribs and possibly heart will also be irradiated. The prescribed dose is either 42.5 Gy in 16 fractions over 22 days, or 45 Gy in 25 fractions over 33 days (extended fractionation) with a boost dose to the tumour bed. The extended fractionation schedule is reserved for patients with a large separation (>24 cm) or significant post-operative changes (induration, oedema, erythema, haematoma or infection). Additional radiation to the tumour bed may be prescribed if the pathological margins are less than 2 mm.

The consensus opinion of radiation oncologists on the breast site team at BC Cancer Agency, Vancouver Centre is that a reduction in the area of skin receiving >80% of the target dose will result in a reduction in the likelihood of moist desquamation. Using modern linear accelerators, the skin on the surface of the breast facing the beam receives some reduction in dose due to the skin sparing effect in high energy x-ray beams. The epidermal layer (acute effects) varies in thickness from 0.03 to 0.3 mm in different regions of the body and the underlying dermal layer (late effects) varies from 1 mm to 3 mm thick. For a 6 MV beam, the maximum dose occurs at a depth of 15 mm and for 10 MV the dose peaks at a depth of 25 mm. Dose to the epidermal layer where the beam enters the breast is approximately 20 to 40% of the peak dose, depending on beam energy and field size.

The total skin dose on the breast surface is the sum of the entrance and exit doses from the two opposing beams. The average total skin dose on medial and lateral breast skin surfaces, in the absence of skin folds, is 50-60% of the prescription dose. Moist desquamation is generally not observed in these areas of the skin.

In the infra-mammary and axilla areas, the skin can be folded inward and is enveloped within target breast tissue. Thus, these areas of skin may receive 100% or more of the prescribed dose. A reduction in moist desquamation may be achieved if the skin folds can be minimized so that dose is reduced in these areas.

The inventors have performed preliminary work looking at surface dose on tissue equivalent phantoms with and without a carbon fibre breast support scoop in place, using a film dosimetry system (EBT3 Gafchromic film and Film-Pro QA software, Ashland Corporation, www.ashland.com) specifically designed to measure skin dose. A 20% to 30% enhancement of the surface dose was found to occur under the carbon fibre scoop in regions of tangential beam incidence. The doses on all areas of the breast surface were < or = to 80% of the prescribed dose for both 6 MV and 10 MV x-ray beam arrangements.

LIST OF ACRONYMS

BCCA British Columbia Cancer Agency
CT Computed Tomography
GSC Genome Sequencing Centre
IMRT Intensity Modulate Radiation Therapy
RTOG Radiation Therapy Oncology Group

INTERPRETATION OF TERMS

Unless the context clearly requires otherwise, throughout the description and the claims:
- "comprise", "comprising", and the like are to be construed in an inclusive sense, as opposed to an exclusive or exhaustive sense; that is to say, in the sense of "including, but not limited to";
- "connected", "coupled", or any variant thereof, means any connection or coupling, either direct or indirect, between two or more elements; the coupling or connection between the elements can be physical, logical, or a combination thereof;
- "herein", "above", "below", and words of similar import, when used to describe this specification, shall refer to this specification as a whole, and not to any particular portions of this specification;
- "or", in reference to a list of two or more items, covers all of the following interpretations of the word: any of the items in the list, all of the items in the list, and any combination of the items in the list;
- the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Where a component (e.g. a member, arm, coupling, radiation source assembly, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An apparatus for supporting a breast for radiation treatment, the apparatus comprising:
   a paddle comprising first and second generally planar faces oriented at a right angle to one another; and
   a support structure connected to hold the paddle at a desired position and orientation, the support structure adjustable to bring the first face against and supporting an inferior side of a patient's breast while the second face is against and supporting a lateral side of the patient's breast.

2. The apparatus according to claim 1 wherein the paddle comprises a curved central section connecting the first and second faces.

3. The apparatus according to claim 2 wherein the central section has a radius of curvature about an axis in the range of 30 mm to 70 mm.

4. The apparatus according to claim 1 wherein the first and second faces have top and bottom edges separated by distances of 5 cm to 15 cm.

5. The apparatus according to claim 1 wherein the second face has a length in a direction parallel to a top edge of the second face that exceeds a distance between the top edge of the second face and a bottom edge of the second face.

6. The apparatus according to claim 1 wherein the paddle is detachably coupled to the support structure.

7. The apparatus according to claim 6 wherein the paddle is one of a pair of paddles made up of first and second paddles wherein the first and second paddles are mirror images of one another.

8. The apparatus according to claim 1 wherein the paddle is made of a carbon fibre composite material.

9. The apparatus according to claim 1 wherein the paddle is made of a material that is free of elements having atomic number higher than 14.

10. The apparatus according to claim 1 wherein the support structure comprises a support bar mountable to a table, the support bar including a portion that extends transversely to the table at an elevation above a top surface of the table.

11. The apparatus according to claim 10 wherein the support structure comprises a hoop having opposed ends mountable to the table and the transversely-extending portion of the support bar is provided by a mid-portion of the hoop.

12. The apparatus according to claim 10 wherein the apparatus comprises a first arm extending at right angles to the support bar and coupled to the support bar by one or more first couplings that allow adjustment of a position of the first arm along the support bar.

13. The apparatus according to claim 12 wherein the one or more first couplings allow longitudinal adjustment of a position of the first arm relative to the support bar.

14. The apparatus according to claim 12 wherein the support structure comprises a second arm extending at right angles to the first arm and coupled to the first arm by one or more second couplings that allow longitudinal adjustment of a position of the second arm.

15. The apparatus according to claim 14 comprising a coupling carried by the second arm, the coupling detachably holding the paddle.

16. The apparatus according to claim 14 wherein the second arm is supported at an angle of 9 to 16 degrees from vertical.

17. The apparatus according to claim 12 wherein the first arm is supported at an angle of 9 to 16 degrees from horizontal.

18. The apparatus according to claim 12 comprising an angled support board extending under the support bar.

19. The apparatus according to claim 18 wherein the first arm extends in a plane that is generally parallel to a top surface of the support board.

20. The apparatus according to claim 10 wherein the support structure comprises carbon fibre composite.

21. The apparatus according to claim 10 wherein the support structure is free of metal.

22. The apparatus according to claim 1 comprising a plurality of radiopaque markers at spaced apart locations on the support structure.

23. The apparatus according to claim 1 comprising indicia on the paddle, the indicia marking spots that may be aligned to fiducial markers on the patient.

24. The apparatus according to claim 23 wherein the indicia comprise first and second holes respectively penetrating the first and second faces of the paddle.

25. A method for preparing a patient to receive radiation treatment, the method comprising:
   arranging the patient in a supine position on a support board angled upwardly toward the patient's head;
   placing a paddle comprising first and second generally planar faces oriented at a right angle to one another against the patient's breast such that the first face of the paddle supports a lateral side of the patient's breast and the second face of the paddle supports an inferior side of the patient's breast.

26. The method according to claim 25 comprising arranging a radiation source next to the patient's breast and aligning the radiation source such that a direction of radiation emission is perpendicular to the first face of the paddle.

27. The method according to claim 26 wherein the radiation source comprises a source of MeV photons.

28. The method according to claim 27 wherein the radiation source is a source of photons having photon energies of at least 10 MeV.

* * * * *